United States Patent [19]

Felix

[11] Patent Number: 4,654,072
[45] Date of Patent: Mar. 31, 1987

[54] HERBICIDAL PHOSPHONOMETHYL AMIDES

[75] Inventor: Raymond A. Felix, Richmond, Calif.

[73] Assignee: Stauffer Chemical Company, Westport, Conn.

[21] Appl. No.: 776,929

[22] Filed: Sep. 17, 1985

[51] Int. Cl.⁴ .................. A01N 57/30; C07F 9/38; C07F 9/40
[52] U.S. Cl. .................. 71/86; 260/502.5 D; 546/24; 558/168; 558/170; 558/174; 558/386; 560/21; 560/39
[58] Field of Search ............ 260/465 D, 940, 941, 260/942, 943, 502.5 D; 560/39, 21; 546/24; 71/86; 558/386, 168, 170, 174

[56] References Cited

U.S. PATENT DOCUMENTS

| | | | |
|---|---|---|---|
| 4,218,235 | 8/1980 | Franz et al. | 71/86 |
| 4,309,562 | 1/1982 | Takahashi et al. | 71/108 |
| 4,364,767 | 12/1982 | Gough | 71/86 |
| 4,427,599 | 1/1984 | Felix | 260/502.5 F |

*Primary Examiner*—Dolph H. Torrence
*Attorney, Agent, or Firm*—Joel G. Ackerman

[57] ABSTRACT

Compounds having the formula

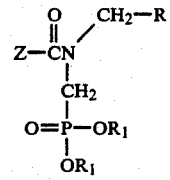

in which R is hydrogen, cyano or —COOR$_2$; R$_1$ is hydrogen or C$_1$-C$_4$ alkyl; R$_2$ is hydrogen or C$_1$-C$_4$ alkyl; and Z is

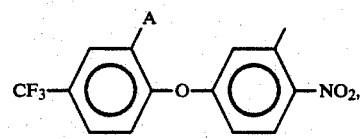

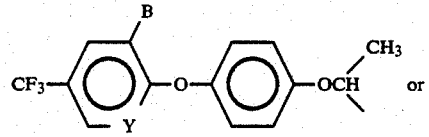 or

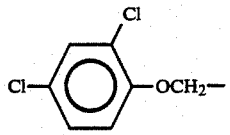

in which A is halogen, B is halogen or hydrogen and Y is nitrogen or —CH—, are herbicides.

15 Claims, No Drawings

HERBICIDAL PHOSPHONOMETHYL AMIDES

This invention relates to novel herbicidal compounds having the formula

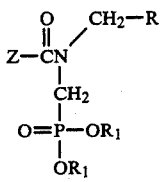

in which R is hydrogen, cyano or —COOR$_2$; R$_1$ is hydrogen or C$_1$–C$_4$ alkyl R$_2$ is hydrogen or C$_1$–C$_4$ alkyl; and Z is

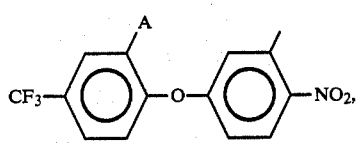

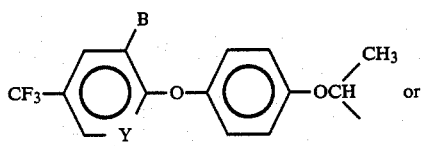

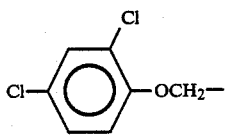

in which A is halogen, B is halogen or hydrogen and Y is nitrogen or —CH—. The term "halogen" includes chloro, fluoro, bromo and iodo.

The compounds of this invention have been found to be active herbicides in possessing herbicidal activity against various species of weeds. In the broadest sense, the term "weed" refers to plants which grow in locations in which they are not desired.

This invention also therefore relates to a method for controlling undesirable vegetation, comprising applying to a locus where control of such vegetation is desired, an herbicidally effective amount of a compound as described herein, and also relates to herbicidal compositions of matter comprising an herbicidally effective amount of a compound as described herein, together with an inert diluent or carrier suitable for use with herbicides.

As used herein the term "herbicide" refers to compounds which adversely control or modify the growth of plants, particularly of undesirable plants. By the term "herbicidally effective amount" is meant an amount of compound which causes an adverse controlling or modifying effect on the growth of plants. The term "plants" is meant to include germinant seeds, emerging seedlings, and established vegetation, including roots and above-ground portions. Such adverse modifying and controlling effects may include all deviations from natural development.

The compounds of this invention are generally prepared analogously to the process described in U.S. Pat. No. 4,425,284, by reacting one equivalent of an appropriately substituted hydrogenated 1,3,5-triazine with 3 equivalents of the appropriately substituted aryl acid halide in a suitable inert solvent such as toluene, methylene chloride or ethylene dichloride. Preferably, the reaction is run at a temperature from about 0° to about 120° C., more preferably from about 40° to about 100° C., and most preferably from about 75° to about 80° C. This reaction step can be run at atmospheric, sub-atmospheric or super-atmospheric pressure, preferably at atmospheric pressure. The resulting chloromethyl amide of the aryl halide is reacted with one equivalent of the appropriate phosphite to prepare the desired compound. The chloromethyl amide may be isolated before reaction with the phosphite or this reaction can be conducted in the same apparatus as the previous step.

Acids (R=COOH; R$_1$=H) are prepared from the corresponding esters by hydrolysis as shown in Example 2.

The following are examples of the preparation of compounds according to this invention.

EXAMPLE I

Preparation of
O,O-Dimethyl-N-carbomethoxymethyl-N-2-[4-(4'-trifluoromethyl)phenoxy]phenoxy-propionyl aminomethyl phosphonate (Compound 2 herein)

In a flask were placed 2.20 grams (g) (0.0067 m) of 1,3,5-tricarbomethoxymethyl hexahydro-1,3,5-triazine and 20 milliliters (ml) of 1,2-dichloroethane. N-[2-<4-(4'-trifluoromethyl)phenoxy>phenoxypyropionyl]-chloride (6.89 g, 0.02 m) was added dropwise and the reaction mixture refluxed 15 minutes. To this mixture was added 2.36 ml (0.02 m) trimethylphosphite. The reaction mixture was allowed to stir at reflux 15 minutes after the addition and cooled at room temperature, washed with water, dried over anhydrous magnesium sulfate and evaporated to dryness under reduced pressure to yield the desired product. The structure was confirmed by infrared and nuclear magnetic resonance spectroscopy.

EXAMPLE II

Preparation of
N-carboxymethyl-N-2[4-(4'-trifluoromethyl)phenoxy]-phenoxy propionyl aminomethyl phosphonic acid (Compound 4 herein)

In a flask were placed 6 g (0.0116 m) O,O-dimethyl-N-[2->4-(4'-trifluoromethyl)phenoxy>phenoxy]propionyl-N-carbomethylmethyl aminomethyl phosphate. To this was added 3.37 ml bromotrimethyl silane (0.0255 m) at 50° C. The mixture was stirred at 50° C. one hour and the volatiles evaporated under reduced pressure. 1.81 ml (0.128 m) iodotrimethyl silane was added to the above product, stirred at room temperature and then evaporated under reduced pressure. Methanol (25 ml) was added and the mixture was heated at reflux one hour and evaporated under reduced pressure to yield 5.3 g of the desired product (a glass). The structure was confirmed by infrared and nuclear magnetic resonance spectroscopy.

The following Table I depicts representative compounds of this invention.

TABLE I $$Z-\overset{\overset{O}{\|}}{C}N\overset{CH_2-R}{\underset{\underset{\underset{OR_1}{|}}{\underset{O=P-OR_1}{|}}}{\overset{|}{CH_2}}}$$

| Cmpd. No. | R | $R_1$ | Z | Physical Constant |
|---|---|---|---|---|
| 1 | H | $CH_3$ | $CF_3$-⟨⟩(Cl)-O-⟨⟩-$NO_2$ | $n_D^{30}$ 1.5386 |
| 2 | $-\overset{\overset{O}{\|}}{C}OCH_3$ | $CH_3$ | $CF_3$-⟨⟩-O-⟨⟩-$\overset{CH_3}{\underset{OCH-}{|}}$ | $n_D^{30}$ 1.5048 |
| 3 | $-C{\equiv}N$ | $CH_3$ | $CF_3$-⟨⟩-O-⟨⟩-$\overset{CH_3}{\underset{OCH-}{|}}$ | $n_D^{30}$ 1.5095 |
| 4 | $-\overset{\overset{O}{\|}}{C}OH$ | H | $CF_3$-⟨⟩-O-⟨⟩-$\overset{CH_3}{\underset{OCH-}{|}}$ | glass |
| 5 | $-C{\equiv}N$ | $CH_3$ | Cl-⟨⟩(Cl)-$OCH_2-$ | $n_D^{30}$ 1.5303 |
| 6 | $-\overset{\overset{O}{\|}}{C}OC_2H_5$ | $CH_3$ | Cl-⟨⟩(Cl)-$OCH_2-$ | $n_D^{30}$ 1.520 |

The compounds listed in the foregoing Table I were tested for herbicidal activity as follows:

Pre-Emergence Herbicide Screening Test

Flats were filled with sandy loan soil containing a fungicide and fertilizer. The soil was leveled and rows of three grassy weeds, four broadleaf weeds and yellow nutsedge (*Cyperus esculentus*), were planted thickly enough so that several seedlings emerged per inch of row. The grassy weeds were: foxtail (*Setaria* spp.), watergrass (*Echinochloa crusgalli*) and wild oat (*Avena fatua*). Broadleaf weeds utilized were annual morning-glory (*Ipomoea purpurea*), velvetleaf (*Alutilon theophrasti*), mustard (*Brassica juncea*), and curly dock (*Rumex crispus*).

The flats were placed in a greenhouse at 70°-85° F. and watered by sprinkling. One day after planting the flats were sprayed with a solution of a test compound at a rate of 80 gallons of solution per acre with the compound being applied at a rate of 4 pounds per acre (4.48 kg/ha).

The solutions of the test compounds were made by weighing out 300 mg of the compound in question into a 120 ml wide-mouth bottle, dissolving it in 50 ml of acetone containing 1% polyoxyethylene sorbitan monolaurate emulsifier and then diluting to 100 ml with water. Additional solvents, not exceeding 5 ml, were used if needed to dissolve the compound.

The flats were returned to the greenhouse after spraying and watered daily by sprinkling. The degree of weed control was estimated and recorded 3 weeks after treatment, as percentage control compared to the growth of the same species in an untreated check flat of the same age.

The percent control is based on the total injury to the plants due to all factors, including inhibited germination, killing of the plant tissue after emergence, stunting, malformation, chlorosis, and other types of injury. The control rating vary from 0 to 100 percent, where 0 represents no effect with growth equal to the untreated control, and 100 represents complete kill.

Post-Emergence Herbicidal Evaluation

The soil was prepared and seeded with the same varieties as described for the pre-emergence test. The flats were placed in the greenhouse at 70°-85° F. and watered by sprinkling. Nine to eleven days after planting, the flats were sprayed on a table at a rate of 80 gallons of solution per acre. The compound was applied at the rate of 4 pounds/acre (4.48 kg/ha). The spray solution was made up similarly to that described for the pre-emergence evaluation.

The flats were returned to the greenhouse after spraying and watered daily without wetting the foliage for three days. Thereafter, they were watered daily by sprinkling. Three weeks after treatment the degree of weed control was estimated and recorded as percentage control compared to the growth of the same species in an untreated check flat of the same age. The percent control ratings were assigned on the same basis as for the pre-emergence evaluation.

The following Table II contains the results of these tests, in terms of average control of the three grasses, four broadleaf weeds, and yellow nutsedge, respectively, in both pre- and post-emergence evaluations.

(Sesbania spp.),. sicklepod (*Cassia obtusifolia* and broadleaf signalgrass (*Brachiaria platyphilla*); grassy weeds were: foxtail, watergrass, wild oat, downy brome (*Bromus tectorum*), annual ryegrass (*Lolium multiflorum*) and shattercane (*Sorghum bicolor*); crops included were: soybean (*Glycine max*), rice (*Oryza sativa*), cotton (*Gossypium herbaceum*), corn (*Zea mays*), wheat (*Triticum aestivum*), milo (*Sorghum vulgare*) and sugarbeets (*Beta vulgaris*). Yellow nutsedge was also included in these tests.

The following Table III contains the results of these tests, in terms of average control of the broadleaf weeds, grassy weeds, and nutsedge, and injury to the crop species, with visual ratings ranging from 0% (no injury) to 100% (complete kill) as compared to untreated control flats.

TABLE III

| | | | Pre-Emergence Evaluation - 2 lb/Acre | | | | | | | | |
|---|---|---|---|---|---|---|---|---|---|---|---|
| Cmpd. No. | Broadleaf weeds | grasses | nutsedge | soybean | corn | rice | cotton | wheat | milo | Sugarbeets | Barley |
| 1 | 73 | 48 | — | — | — | — | — | 60 | — | 85 | 55 |
| 2 | 10 | 83 | 0 | 15 | 65 | 97 | 0 | 35 | 97 | 15 | — |

TABLE II

| | Pre-Emergence Control | | | Post-Emergence control | | |
|---|---|---|---|---|---|---|
| Compound Number | grasses | broadleaf weeds | nutsedge | grasses | broadleaf weeds | nutsedge |
| 1 | 70 | 41 | 50 | 80 | 100 | 50 |
| 2 | 73 | 0 | 0 | 100 | 0 | 0 |
| 3 | 87 | 0 | 0 | 97 | 0 | 0 |
| 4 | 72 | 23 | 0 | 100 | 75 | 0 |
| 5 | 0 | 34 | 0 | 0 | 95 | 0 |
| 6 | 17 | 0 | 0 | 28 | 89 | 0 |

Pre-Emergence multi-weed/multi-crop evaluation

Compounds 1 and 2 were evaluated at an application rate of 2.0 lb. active ingredient/acre (2.24 kg/ha) for preemergence activity against a number of weed and crop species. The procedure was generally similar to the preemergence evaluation described above. Species utilized in evaluating Compound 1 were: grassy weeds: poverty brome (*Bromus sterilis*), blackgrass (*Alopecurus myosuroides*), perennial ryegrass (*Lolium perenne*), wild oats (*Avena fatua*); broadleaf weeds: wild mustard (*Sinapis arvensis*), curly dock (*Rumex crispus*), bedstraw (*Galium aparine*); crops: sugarbeets (*Beta vulgaris*), barley (*Hordeum vulgare*), and wheat (*Triticum aestivum*). For Compound 2 broadleaf weed species utilized were annual morningglory, velvetleaf, mustard, sesbania Post-Emergence Multi-weed/Multi-crop Evaluation Compounds 1, 2, 5 and 6 were evaluated at various application rates ranging from 0.25 to 2.0 pounds per acre (0.28 to 2.24 kg/ha) for post-emergent activity. The procedure was generally similar to the post-emergence evaluation described above. Some tests, as indicated, included only broadleaf or only grassy weeds. Broadleaf weed species utilized were variously annular morningglory, velvetleaf, mustard, sesbania, sicklepod, broadleaf signalgrass, redroot pigweed (*Amaranthus retroflexus*) and cocklebur (*Xanthium pennsylvanicum*), Grassy weeds utilized were: foxtail, watergrass, wild oat, downy brome, annual ryegrass and shattercane. Crops included were: soybean, rice, cotton, corn, winter wheat, milo and sugarbeet.

The following Table IV contains the results of these tests, in terms of average control of the broadleaf weeds, grassy weeds, and nutsedge, and injury to the crop species, with visual ratings ranging from 0% (no injury) to 100% (complete kill) as compared to untreated control flats.

TABLE IV

| | | | | Post-Emergent Evaluation | | | | | | | |
|---|---|---|---|---|---|---|---|---|---|---|---|
| Cmpd. No. | lb/A | Broadleaf weeds | grasses | nutsedge | soybean | corn | rice | cotton | wheat | milo | Sugarbeets |
| 1 | 2.00 | 95 | — | 65 | 20 | 25 | 85 | 100 | 25 | 70 | 100 |
| | 0.25 | 73 | — | — | 15 | 0 | 0 | 90 | 0 | 45 | 60 |
| 2 | 2.00 | 44 | 74 | 0 | 50 | 80 | 65 | 0 | 20 | 95 | 0 |
| 2 | 1.00 | — | 69 | 0 | 25 | 70 | 35 | 0 | 15 | 30 | 0 |
| 2 | 0.50 | — | 33 | 0 | 25 | 20 | 20 | 0 | 0 | 30 | 0 |
| 2 | 0.25 | — | 0 | 0 | 25 | 0 | 20 | 0 | 0 | 15 | 0 |
| 5 | 2.00 | 79 | 0 | 0 | 90 | 0 | 0 | 90 | 0 | 0 | 85 |
| 5 | 1.00 | 71 | 0 | 0 | 90 | 0 | 0 | 90 | 0 | 0 | 70 |
| 5 | 0.50 | 69 | 0 | 0 | 60 | 0 | 0 | 80 | 0 | 0 | 40 |
| 5 | 0.25 | 23 | 0 | 0 | 25 | 0 | 0 | 60 | 0 | 0 | 10 |
| 6 | 2.00 | 89 | 6 | 0 | 80 | 0 | 30 | 80 | 0 | 35 | 100 |
| 6 | 1.00 | 81 | — | 0 | 70 | 0 | 20 | 65 | 0 | 0 | 60 |

In practice, a pure compound can be used as a herbicide. However, in general, the compounds are first formulated with one or more inert carriers or diluents suitable for herbicidal use, before being applied.

The compositions of formulations, including a compound as described herein, may exist in any one of a number of solid or liquid forms. Examples of solid forms are dusts, granules, tablets, powders and the like. Examples of liquid forms are emulsifiable concentrates, flowables and pastes. Such compositions may contain, in addition to the active compound or compounds, various carriers or diluents; surface active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcium carbonate, silica, kieselguhr, clay, etc.; ground synthetic minearls such as various silicates and aluminosilicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Wettable powders, flowables, and pastes are obtained by mixing and grinding an active compound with one or more dispersing agents and/or solid carriers or diluents. Also included may be wetting agents and/or dispersing agents, for example, lignins, methyl cellulose, naphthalene-sulfonic acid derivatives, fatty alcohol sulfates and various types of alkali and alkaline earth metal salts of fatty acids.

Emulsifiable concentrates are generally obtained by dissolving the active compound in an organic solvent, for example, butanol cyclohexanone, xylenes, or higher boiling aromatic hydrocarbons. To obtain suspensions or emulsions in water, wetting agents are generally also added.

It is possible to use highly concentrated liquid compositions containing up to about 95% by weight of the active compound, or even the active compound alone for those compounds which are liquids, when applying the compound in the form of a finely divided liquid by use of various atomizing equipment, for example by airplane crop spraying techniques. For other purposes, however, the various types of compositions which can be utilized for these compounds will contain varying amounts of the compound according to the type of composition and the intended use.

In general, compositions may contain from 0.1 to 95% of the active compound, more preferably from 0.5 to 90%. Some typical compositions will contain an active compound as follows: wettable powders, flowables and pastes—20 to 90% active compound; oil suspensions, emulsions, solutions and emulsifiable concentrates—5 to 90% active compound; aqueous suspensions—10 to 50% active compound; dusts and powders—1 to 25% active compound; granules and pellets—1 to 20% active compound.

The rate of application of the active compound to a locus to be controlled will depend on the nature of the seeds and plants to be controlled and will vary from about 0.05 to about 50 pounds per acre (about 0.06 to about 56 kg/ha).

In addition to the active compound and the various agents utilized in preparing compositions and formulations mentioned above, such compositions may also contain one or more other active compounds of the type mentioned herein as well as other pesticidal agents, such as herbicides, fungicides, insecticides, acaricides, nematocides, bactericides, and plant growth regulators. Such compositions may also contain soil disinfectants or fumigants and may further contain fertilizers, thus making it possible to provide multi-purpose compositions containing one or more of the compounds described herein as well as, optionally, other pesticides and also fertilizers, all intended and formulated for use at the same locus.

Compositions containing one or more of the active compounds described, in a herbicidally effective amount, may be applied to the plant or locus to be controlled in any conventional manner. Thus, powders and various liquid compositions containing the active compound can be applied by the use of power dusters, boom and hand sprayers and spray dusters, or applied from airplanes as mists or sprays. When applied in the latter method they may be effective in very low dosages. To modify or control growth of germinating seeds or emerging seedlings liquid compositions may be applied to the soil with conventional methods and may be distributed in the soil to a depth of one-half inch below the soil surface. The compositions need not be admixed with the soil particles but can be applied merely by sprinkling on the surface of the soil.

Compositions including active compounds may also be applied by addition to irrigation waters supplied to the field to be treated. This method of application permits penetration of the compounds into the soil as the water is absorbed therein.

| EXAMPLES OF TYPICAL COMPOSITIONS | | | |
|---|---|---|---|
| Ingredient | Weight % | | |
| Oil | | | |
| Compound 1 | 1 | | |
| Oil solvent-heavy aromatic naphtha | 99 | | |
| Total | 100 | | |
| Emulsifiable Concentrate | | | |
| Compound 2 | 50 | | |
| Kerosene | 45 | | |
| Emulsifying agent (mixture of long chain ethoxylated polyethers with long chain sulfonate) | 5 | | |
| Total | 100 | | |
| Emulsifiable Concentrate | | | |
| Compound 3 | 90 | | |
| Kerosene | 5 | | |
| Emulsifying agent (mixture of long chain ethoxylated polyethers with long chain sulfonate) | 5 | | |
| Total | 100 | | |
| Dusts and/or Powders | | | |
| Ingredient | Wt. % | Wt. % | Wt. % |
| Compound 4 | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| Total | 100.0 | 100.0 | 100.0 |

What is claimed is:
1. A compound having the formula

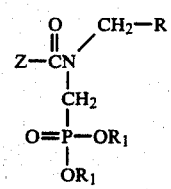

in which R is hydrogen, cyano or —COOR$_2$; R$_1$ is hydrogen or C$_1$-C$_4$ alkyl; R$_2$ is hydrogen or C$_1$-C$_4$ alkyl; and Z is

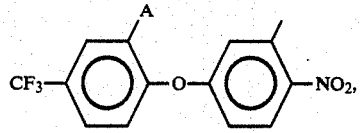

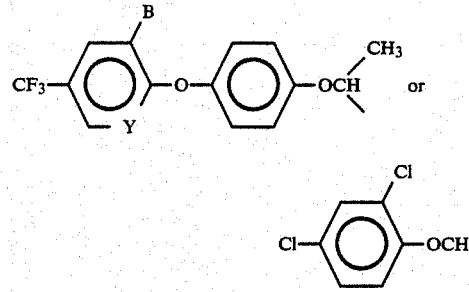

in which A is halogen, B is halogen or hydrogen and Y is nitrogen or —CH— provided that if Z is

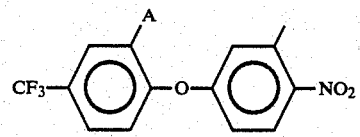

then R is hydrogen or cyano.

2. A compound according to claim 1 in which R is cyano, R$_1$ is methyl and Z is

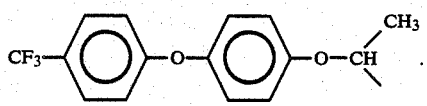

3. A compound according to claim 1 in which R is carbomethoxy, R$_1$ is methyl and Z is

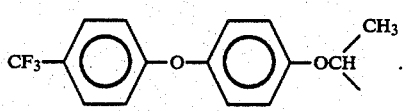

4. A compound according to claim 1 in which R is carboxyl, R$_1$ is hydrogen and Z is

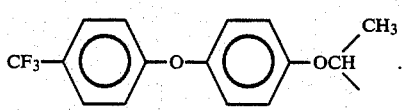

5. A compound according to claim 1 in which R is hydrogen, R$_1$ is methyl and Z is

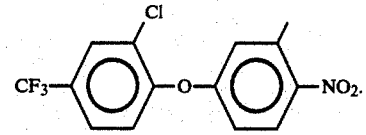

6. A compound according to claim 1 which R is cyano, R$_1$ is methyl and Z is

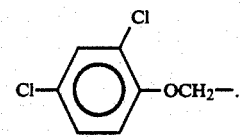

7. A compound according to claim 1 which R is carboethoxy, R$_1$ is methyl and Z is

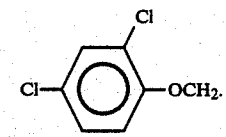

8. A method of controlling undesirable vegetation comprising applying to a locus where control is desired an herbicidally effective amount of a compound having the formula

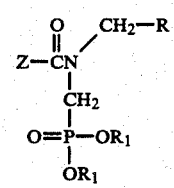

in which R is hydrogen, cyano or —COOR$_2$; R$_1$ is hydrogen or C$_1$-C$_4$ alkyl; R$_2$ is hydrogen or C$_1$-C$_4$ alkyl; and Z is

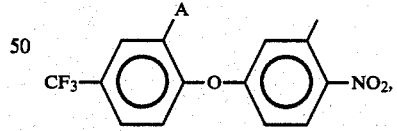

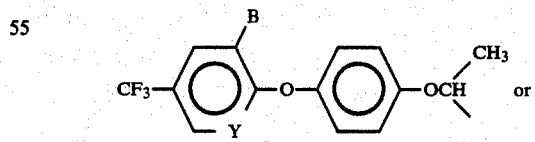

in which A is halogen, B is halogen or hydrogen and Y is nitrogen or —CH— provided that if Z is

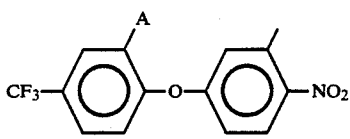

then R is hydrogen or cyano.

9. A method according to claim 8 in which R is cyano, $R_1$ is methyl and Z is

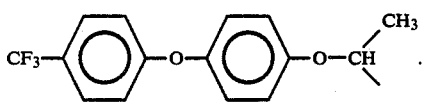

10. A method according to claim 8 in which R is carbomethoxy, $R_1$ is methyl and Z is

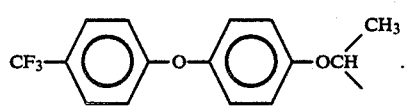

11. A method according to claim 6 in which R is carboxyl, $R_1$ is hydrogen and Z is

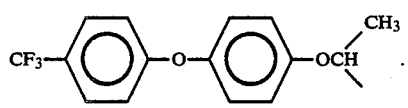

12. A method according to claim 8 in which R is hydrogen, $R_1$ is methyl and Z is

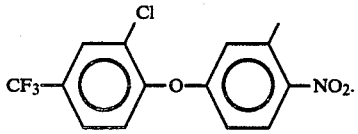

13. A method according to claim 8 in which R is cyano, $R_1$ is methyl and Z is

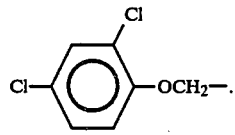

14. A method according to claim 8 in which R is carboethoxy, $R_1$ is methyl and Z is

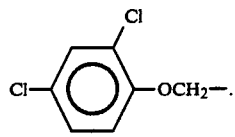

15. An herbicidal composition comprising:
(a) an herbicidally effective amount of a compound having the formula

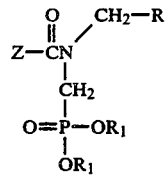

in which R is hydrogen, cyano or —$COOR_2$; $R_1$ is hydrogen or $C_1$–$C_4$ alkyl; $R_2$ is hydrogen or $C_1$–$C_4$ alkyl; and Z is

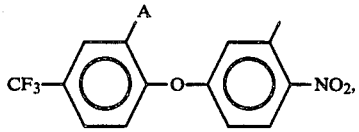

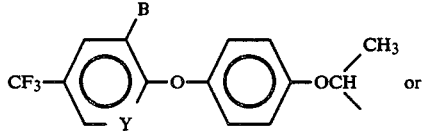 or

in which A is halogen, B is halogen or hydrogen and Y is nitrogen or —CH— provided that if Z is

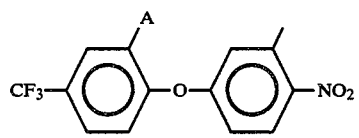

then R is hydrogen or cyano; and
(b) an herbicidally suitable inert diluent or carrier.

* * * * *